US009918870B2

(12) United States Patent
Hedman et al.

(10) Patent No.: US 9,918,870 B2
(45) Date of Patent: *Mar. 20, 2018

(54) TISSUE CROSSLINKING FOR TREATMENT OF SNORING AND OBSTRUCTIVE SLEEP APNEA

(71) Applicant: Orthopeutics, L.P., Lexington, KY (US)

(72) Inventors: Thomas P. Hedman, Lexington, KY (US); Pawel Slusarewicz, Lexington, KY (US)

(73) Assignee: Orthopeutics, L.P., Lexington, KY (US)

( * ) Notice: Subject to any disclaimer, the term of this patent is extended or adjusted under 35 U.S.C. 154(b) by 39 days.

This patent is subject to a terminal disclaimer.

(21) Appl. No.: 14/869,420

(22) Filed: Sep. 29, 2015

(65) Prior Publication Data

US 2016/0015555 A1   Jan. 21, 2016

Related U.S. Application Data

(63) Continuation of application No. 13/704,220, filed as application No. PCT/US2011/042197 on Jun. 28, 2011, now Pat. No. 9,192,507, said application No. 13/704,220 is a continuation-in-part of application No. 10/230,671, filed on Aug. 29, 2002, now Pat. No. 9,084,772.

(60) Provisional application No. 60/316,287, filed on Aug. 31, 2001, provisional application No. 61/359,202, filed on Jun. 28, 2010.

(51) Int. Cl.
| | |
|---|---|
| *A61F 5/56* | (2006.01) |
| *A61K 31/352* | (2006.01) |
| *A61K 31/11* | (2006.01) |
| *A61M 5/178* | (2006.01) |
| *A61M 11/00* | (2006.01) |
| *A61M 31/00* | (2006.01) |
| *A61M 16/04* | (2006.01) |

(52) U.S. Cl.
CPC ............... *A61F 5/56* (2013.01); *A61F 5/566* (2013.01); *A61K 31/11* (2013.01); *A61K 31/352* (2013.01); *A61M 5/178* (2013.01); *A61M 11/00* (2013.01); *A61M 16/0406* (2014.02); *A61M 31/00* (2013.01); *A61M 2202/0007* (2013.01); *A61M 2205/04* (2013.01); *A61M 2210/065* (2013.01); *A61M 2210/0618* (2013.01); *A61M 2210/1028* (2013.01)

(58) Field of Classification Search
None
See application file for complete search history.

(56) References Cited

U.S. PATENT DOCUMENTS

| | | | |
|---|---|---|---|
| 6,375,672 B1 | 4/2002 | Aksan et al. | |
| 6,439,238 B1 | 8/2002 | Brenzel et al. | |
| 6,726,920 B1 | 4/2004 | Theeuwes et al. | |
| 6,812,211 B2 | 11/2004 | Slivka et al. | |
| 7,435,722 B2 * | 10/2008 | Hedman ............... | A61K 9/0019 514/23 |
| 8,022,101 B2 | 9/2011 | Hedman | |
| 8,119,599 B2 | 2/2012 | Hedman | |
| 8,153,600 B2 | 4/2012 | Hedman | |
| 8,198,248 B2 | 6/2012 | Hedman | |
| 8,211,936 B2 | 7/2012 | Hedman | |
| 8,283,322 B2 | 10/2012 | Hedman | |
| 8,450,276 B2 | 5/2013 | Hedman | |
| 9,192,507 B2 * | 11/2015 | Hedman ................. | A61F 5/566 |
| 2002/0037310 A1 | 3/2002 | Jonn et al. | |
| 2003/0049301 A1 | 3/2003 | Hedman | |
| 2003/0104041 A1 | 6/2003 | Hsu et al. | |
| 2007/0202143 A1 | 8/2007 | Hedman | |
| 2010/0040593 A1 | 2/2010 | Hedman et al. | |
| 2011/0060070 A1 | 3/2011 | Dias | |
| 2011/0082199 A1 | 4/2011 | Hedman | |
| 2011/0106243 A1 | 5/2011 | Wilhelmina et al. | |
| 2013/0085569 A1 | 4/2013 | Hedman | |
| 2013/0087155 A1 | 4/2013 | Hedman | |

FOREIGN PATENT DOCUMENTS

| | | | | |
|---|---|---|---|---|
| DE | 4412190 | * | 10/1995 | ............. A61K 38/22 |
| WO | 2010/001149 A2 | | 1/2010 | |

OTHER PUBLICATIONS

English machine translation of DE4412190 (1995) downloaded from EPO patent translate.*
U.S. Appl. No. 15/180,552, filed Jun. 2016, Brown et al.*
Pang et al., "Modified cautery-assisted palatal stiffening operation: New method for treating snoring and mild obstructive sleep apnea" Otolaryngology—Head and Neck Surgery vol. 136 pp. 823-826 (Year: 2007).*
Kurniawan, L., et al. (2009) Formation of Wheat-Protein-Based Biomaterials through Polymer Grafting and Crosslinking Reactions to introduce New Functional Properties. Macromol. Biosci. 9(1): 93-101.
Teng, W., et al, (2011) Physical crosslinking modulates sustained drug relese from recombinant silk-elastin like protein polymer for ophthalmic applications. J. Cont. Release. 156(2): 186-94.
Lowe, A.A. 1994. Dental appliances for the treatment of snoring and/ or obstructive steep apnea. In Principles and practice of sleep medicine. M.Kryger, T.Roth, and W.Dement, editors. WB Saunders Co., 722-735.
Mahdavi, A., L.Ferreira, C.Sundback, J.W.Nichol, E.P.Chan, D.J. Carter, C.J.Bettinger, S.Patanavanich, L.Chignozha, E.Ben-Joseph, A.Galakatos, H.Pryor, I.Pomerantseva, P.T.Masiakos, W.Faquin, A.Zumbuehl, S.Hong, J.Borenstein, J.Vacanti, R.Langer, and J.M. Karp. 2008. A biodegradable and biocompatible gecko-inspired tissue adhesive. Proc. Natl. Acad. Sci, U. S. A. 105:2307-2312.

(Continued)

*Primary Examiner* — Eric Olson
(74) *Attorney, Agent, or Firm* — Berliner & Associates

(57) ABSTRACT

A method of treating snoring and/or OSA in a subject in need of such treatment. The method includes crosslinking proteins of the subject's soft palate tissue or pharynx tissue. The crosslinking can occur by contacting the soft palate or pharynx tissue with a crosslinking reagent. In addition, the crosslinking can occur without heating, contracting or denaturing of the tissue, or any combination thereof.

18 Claims, 1 Drawing Sheet

(56) References Cited

OTHER PUBLICATIONS

Romanow, J.H. and P.J.Catalano, 2006. Initial U.S. pilot study: palatal implants for the treatment of snoring. Otolaryngol, Head Neck Surg. 134:551-557.
Zhai, W., J.Chang, K.Lin, J.Wang, Q.Zhao, and X.Sun. 2006. Crosslinking of decellularized porcine heart valve matrix by procyanidins. Biomaterials 27:3684-3690.
Schmidt-Novara, W., A.Lowe, L.Wiegand, R.Cartwright, F.Perez-Guerra, and S. Menn. 1995. Oral appliances for the treatment of snoring and obstructive sleep apnea: a review. Sleep 18:501-510.
Singhal, A.R., C.M.Agrawal, and K.A.Athanasiou. 1996. Salient Degradation Features of a 50:50 PLA/PGA Scaffold for Tissue Engineering. Tissue Eng 2:197-207.
Slusarewicz, P., K.Zhu, and T.Hedman. 2010a. Kinetic characterization and comparison of various protein crosslinking reagents for matrix modification. J. Mater. Sci. Mater, Med. 21:1175-1181.
Slusarewicz, P., et al., 2010, Natural Product Communications; Kinetic Analysis of Genipin Degradation in Aqueous Solution; vol. 5, No. 12, 1853-1858.
Slusarewicz, P., K.Zhu, B.Kirking, J.Toungate, and T.Hedman. 2010c. Optimization of Protein Crosslinking Formulations for the Treatment of Degenerative Disc Disease. Spine in Press.
Sung, H.W., Y. Chang, C.T.Chiu, C.N.Chen, and H.C.Liang. 1999a. Crosslinking characteristics and mechanical properties of a bovine pericardium fixed with a naturally occurring crosslinking agent. J. Biomed. Mater. Res. 47:116-126.
Sung, H.W., Y.Chang, C.T.Chiu, C.N.Chen, and H.C.Liang. 1999b. Mechanical properties of a porcine aortic valve fixed with a naturally occurring crosslinking agent. Biomaterials 20:1759-1772.
Sung, H.W., I.L.Liang, C.N.Chen, R.N. Huang, and H.F.Liang, 2001. Stability of a biological tissue fixed with a naturally occurring crosslinking agent (genipin). J. Biomed. Mater. Res. 55:538-546.
Tang, S.Y., A.D.Sharan, and D.Vashishth. 2008. Effects of collagen crosslinking on tissue fragility. Clin. Biomech. (Bristol. , Avon.) 23:122-123.
Vasudev, S.C. and T.Chandy. 1997. Effect of alternative crosslinking techniques on the enzymatic degradation of bovine pericardia and their calcification. J. Biomed. Mater. Res. 35:357-369
Verzijl, N., J.De Groot, Z.C.Ben, O.Brau-Benjamin, A.Maroudas, R.A.Bank, J.Mizrahi, C.G.Schalkwijk, S.R.Thorpe, J.W.Baynes, J.W.Bijlsma, F.P.Lafeber, and J.M.te Koppele. 2002. Crosslinking by advanced glycation end products increases the stiffness of the collagen network in human articular cartilage: a possible mechanism through which age is a risk factor for osteoarthritis. Arthritis Rheum. 46:114-123.
Wagner, D.R., K.M.Reiser, and J.C.Lotz. 2006. Glycation increases human annulus fibrosus stiffness in both experimental measurements and theoretical predictions. J. Biomech. 39:1021-1029.
Wu, X., L.Black, G,Santacana-Laffitte, and C.W.Patrick, Jr. 2007. Preparation and assessment of glutaraldehyde-crosslinked collagen-chitosan hydrogels for adipose tissue engineering. J. Biomed. Mater. Res. A 81:59-65.
Yang, S.H., C.K.Hsu, K.C.Wang, S.M.Hou, and F.H.Lin. 2005. Tricalcium phosphate and glutaraldehyde crosslinked gelatin incorporating bone morphogenetic protein—a viable scaffold for bone tissue engineering. J. Biomed. Mater. Res. B Appl. Biomater. 74:468-475.
Yerramalli, C.S., A.I.Chou, G.J.Miller, S.B.Nicoll, K.R.Chin, and D.M.Elliott. 2007. The effect of nucleus pulposus crosslinking and glycosaminoglycan degradation on disc mechanical function. Biomech. Model. Mechanobiol. 6:13-20.

Agrawal, C.M. and K.A.Athanasiou, 1997. Technique to control pH in vicinity of biodegrading PLA-PGA implants. J. Biomed. Mater, Res. 38:105-114.
Athanasiou; K.A., A.R.Singhal, C.M.Agrawal, and B.D,Boyan. 1995. In vitro degradation and release characteristics of biodegradable implants containing trypsin inhibitor. Clin. Orthop. Relat Res.272-281.
Blumen, M.B., S.Dahan, B.Fleury, C.Hausser-Hauw, and F.Chabolle. 2002. Radiofrequency ablation for the treatment of mild to moderate obstructive sleep apnea. Laryngoscope 112:2086-2092.
Brietzke, S.E. and E.A.Mair. 2001. injection snoreplasty: how to treat snoring without all the pain and expense. Otolaryngol. Head Neck Surg. 124:503-510.
Brietzke, S.E. and E.A.Mair. 2003. Injection snoreplasty: extended follow-up and new objective data. Otolaryngol. Head Neck Surg. 128:605-615.
Brietzke, S.E. and E.A.Mair. 2004. Injection snoreplasty: investigation of alternative sclerotherapy agents, Otolaryngol. Head Neck Surg. 130:47-57.
Catalano, P., Y.H.Goh, and J.Romanow. 2007. Additional palatal implants for refractory snoring. Otolaryngol. Head Neck Surg. 137:105-109.
Charulatha, V. and A.Rajaram. 2003. Influence of different crosslinking treatments on the physical properties of collagen membranes. Biomaterials 24:759-767.
Chuang, S.Y., R.M.Odono, and T.P.Hedman. 2007. Effects of exogenous crosslinking on in vitro tensile and compressive moduli of lumbar intervertebral discs. Clin. Biomech. 22:14-20.
Fischer, Y., B.Hafner, and W.J.Mann. 2000. [Radiofrequency ablation of the soft palate (somnoplasty). A new method in the treatment of habitual and obstructive snoring]. HNO 48:33-40.
Friedman, M., R.Vidyasagar, D.Bliznikas, and N.J.Joseph. 2006. Patient selection and efficacy of pillar implant technique for treatment of snoring and obstructive sleep apnea/hypopnea syndrome. Otolaryngol. Head Neck Surg. 134:187-196.
Gratzer, P.F. and J.M.Lee. 2001. Control of pH alters the type of cross-linking produced by 1-ethyl-3-(3-dimethylaminopropyl)-carbodiimide (EDC) treatment of acellular matrix vascular grafts. J. Biomed. Mater. Res. 58:172-179.
Guilleminault, C., R.Stoohs, and S.Duncan. 1991. Daytime sleepiness in regular snorers. Chest 99:40-49.
Guilleminault, C., A.Tilkian, and W.C.Dement. 1976. The sleep apnea syndromes. Annu. Rev. Med. 27:465-484.
Han, B., J.Jaurequi, B.W.Tang, and M.E,Nimni. 2003. Proanthocyanidin: a natural crosslinking reagent for stabilizing collagen matrices. J. Biomed. Mater. Res. A 65:118-124.
Hedman, T.P., H.Saito, C.Vo, and S.Y.Chuang. 2006. Exogenous cross-linking increase the stability of spinal motion segments. Spine 31:480-485.
Hoffmann, B., D.Seitz, A.Mencke, A.Kokott, and G.Ziegler. 2009. Glutaraldehyde and oxidised dextran as crosslinker reagents for chitosan-based scaffolds for cartilage tissue engineering. J. Mater. Sci. Mater. Med. 20:1495-1503.
Hunter, S.A., F.R.Noyes, B.Haridas, M.S.Levy, and D.L.Butler. 2005. Meniscal material properties are minimally affected by matrix stabilization using glutaraldehyde and glycation with ribose. J. Orthop. Res. 23:555-561.
Jonn,J.Y., J.Bobo, J.Quintero, and J.P.Moseley. Absorbable adhesive compositions. [6620846]. 2000. US. Ref Type: Patent.
Klapperich, C.M., C.L.Noack, J.D.Kaufman, L.Zhu, L.Bonnaillie, and R.P.Wool. 2009. A novel biocompatible adhesive incorporating plant-drived monomers. J. Biomed. Mater. Res. A 91:378-384.

* cited by examiner

TISSUE CROSSLINKING FOR TREATMENT OF SNORING AND OBSTRUCTIVE SLEEP APNEA

CROSS-REFERENCE TO RELATED APPLICATIONS

This application is a continuation of application Ser. No. 13/704,220, filed on Dec. 13, 2012, which is a national phase of PCT/US2011/042197, filed on Jun. 28, 2011, which claims priority to Provisional Patent Application No. 61/359,202, filed on Jun. 28, 2010. application Ser. No. 13/704,220 is also a continuation-in-part of application Ser. No. 10/230,671, filed on Aug. 29, 2002, which claims the benefit of Provisional Patent Application No. 60/316,287, filed on Aug. 31, 2001. All of the foregoing applications are incorporated by reference herein.

BACKGROUND

Field of the Invention

This invention relates to the treatment of sleep-related breathing disorders such as snoring and obstructive sleep apnea.

Related Art

Snoring is a condition that affects people of all ages, but is more common in men once they reach middle-age and in overweight women (Schmidt-Nowara et al., 1995). It is frequently associated with the more serious, and sometimes life-threatening, obstructive sleep apnea (OSA). OSA is a condition where breathing is temporarily interrupted during sleep by obstruction of the airway resulting in episodes of hypoxia. Less serious effects of OSA include sleepiness and lethargy, but if left untreated, it can lead to more serious respiratory and cardiovascular complications (Guilleminault et al., 1976). Although not all snorers suffer from OSA, excessively loud snoring is one of the symptoms of the condition. A second form of sleep apnea, central sleep apnea (CSA) is distinguished from OSA because its underlying cause is neurological and not physical.

Snoring poses not only an inconvenience with regard to the disruption of the sleep-cycle of the sufferer's partner, but can also lead to sleep-deprivation in the sufferer due to repeated arousals from upper respiratory tract resistance even in non-apneic individuals in a condition known as upper airway resistance syndrome (Guilleminault et al., 1991). Such sleep-cycle disruption leads to daytime lethargy and drowsiness and results in a substantial decrease in the quality of life of the sufferer.

Both snoring and OSA are conditions of complex and incompletely understood etiology, but both are the result of obstructed flow due to abnormalities in the geometry of the air passages. In the case of snoring, this abnormal flow results in the vibration of soft tissues in the throat (primarily the soft palate) leading to the generation of sound. In the case of OSA, airflow is so restricted that it ceases intermittently. Some of the morphological features that can contribute to both conditions include; an enlarged tongue volume, a receding jaw that alters the geometry of the pharynx, an enlarged uvula, a lack of muscle tone in the throat leading to a more collapsible pharynx. Repeated trauma to the upper airway tissues due to snoring can damage muscle fibers and peripheral nerve fibers which further impairs muscle stabilization and increases the tendency for obstruction.

Treatments for both snoring and OSA have fallen into two broad classes (Sanders, 1990), namely, surgery and the use of various oral appliances. Surgery aims to modify the geometry of various parts of the respiratory tract, thereby facilitating the smoother passage of air. Procedures include reconstruction of the facial skeleton, tracheostomy, and surgery of the soft palate and/or the pharynx (e.g. uvulopalatopharyngoplasty). Oral appliances are worn during sleep and generally divided into two classes (Lowe, 1994). Mandibular advancing devices are custom-molded to fit the dental profile of the patient and designed to alter the geometry of the throat by pushing forward the lower jaw, thereby widening the air passage. Tongue retaining devices are designed to maintain the tongue in an anterior position to minimize its effect in restricting air flow. In the case of OSA, a third class of device has been developed to provide continuous positive air pressure (CPAP) to the patient. By increasing the pressure of the air breathed in by the patient, CPAP devices help to counter the narrowing of the air passage that leads to OSA.

All of the devices described above can be either inconvenient or uncomfortable to use, and while they all provide some level of efficacy (Schmidt-Nowara et al., 1995), patient compliance can be an issue. In addition, the surgical procedures outlined above range from being moderately to highly invasive and inconvenient.

More recently, three less invasive surgical procedures have been or are being developed for the treatment of snoring.

1. Radiofrequency ablation depends on the use of electromagnetic radiation to heat regions of the soft palate to a temperature of 77-85° C., resulting in vaporization of tissue plus shrinkage of at least some of the remaining tissue and relief of airway obstruction (Fischer et al., 2000). In addition, the damage caused by heating results in the formation of scar tissue that stiffens the palate and reduces its propensity to vibrate in response to the passage of air. This technique has also been reported to have some efficacy in cases of mild to moderate OSA (Blumen et al., 2002). It would be expected, due to the heat denaturation of the remaining target tissue, that the remaining tissue will have inferior mechanical properties, inferior molecular and micro-structural geometry, and eventual loss of some initial treatment-related benefits.

2. Injection of sclerosants such as sodium tetradecyl sulfate into the soft palate results in fibrosis and the formation of scar tissue in a procedure known as Snoreplasty (Brietzke and Mair, 2004; Brietzke and Mair, 2003; Brietzke and Mair, 2001). As in RF ablation, this scar tissue stiffens the palate and helps to prevent vibration. But also, as in RF ablation, this procedure would be associated with a decline in mechanical properties as well as molecular and microstructural structural integrity leading to an eventual loss of some initial treatment-related benefits.

3. The Pillar procedure seeks to relieve snoring by stiffening via the implantation of small fibrous strips into the soft palate using a relatively simple in-patient procedure (Catalano et al., 2007; Romanow and Catalano, 2006; Friedman et al., 2006). The strips themselves serve to physically stiffen the soft palate, but also induce subsequent scar formation that further enhances the stiffening of the tissue. To the extent that this procedure induces scar stiffening, it would be associated with contributing to the decline in mechanical properties of arguably overloaded and already degraded tissues leading to an eventual loss of some initial treatment-related benefits. In addition one would expect that the tissue-material interface could potentially be the site for micro-motion, wear, particle-release, inflammatory or cellular response, and/or tissue damage.

The underlying principal of these three procedures is the stiffening of the soft palate to increase its damping ratio and thereby ameliorate its vibration as air passes over it. While this approach may be generally effective in ameliorating or eliminating snoring, albeit with the numerous long-term concerns noted above, its success in treating OSA is more varied due to the accompanying long-term tissue degradation and the more diverse nature of the etiology of OSA. Nevertheless, some of these treatments have been demonstrated to exhibit some efficacy in some OSA patients (Blumen et al., 2002; Friedman et al., 2006).

SUMMARY

In accordance herein, treatment is achieved by chemical crosslinking of various soft tissues of the respiratory tract. This crosslinking can alter the mechanical properties of the tissues and thereby render them less susceptible to vibration or collapse during sleep, and less susceptible to mechanical degradation or fatigue.

Thus, in one aspect, a treatment for snoring and/or OSA is provided which includes the crosslinking of soft palate using protein crosslinking reagents, with no associated heating, contraction, inducing fibrosis or denaturation of the tissue in some embodiments. The treatment modifies the mechanical properties of the tissue in order to increase its damping ratio, reduce its oscillation magnitudes and vibration, or increase tissue strength, resilience (energy required to create a non-recoverable deformation), toughness (energy required to fail the tissue), and/or fatigue resistance (durability), or any combination thereof.

In another aspect, crosslinking of the outer fibrous layer of the pharynx is provided in order to stabilize, strengthen, or increase, or any combination thereof, the fatigue resistance of the tissue and help prevent or reduce its collapse in sufferers of OSA.

In a further aspect, a method of treating snoring and/or OSA in a subject in need of such treatment is provided. The method includes augmenting the crosslinking of proteins of the subject's soft palate tissue or pharynx tissue. In some embodiments, the crosslinking comprises contacting the soft palate or pharynx tissue with a crosslinking reagent. In any embodiment, crosslinking can occur without heating, contracting inducing fibrosis, or denaturing of the tissue, or any combination thereof. Also, in any embodiment, the crosslinker can be delivered to the tissue via injection, spaying, a patch, a strip-type delivery device, or any combination thereof. In addition, an aerosol delivery device, a patch, or a strip-type delivery device comprising a crosslinking reagent is also provided, where the aerosol device, patch or strip-type delivery device is adapted for use with soft palate or pharynx tissue. The term "treating" means promoting or enhancing the well being of the subject with respect to snoring and/or OSA, including reducing the severity of one or more symptoms associated with snoring and/or OSA.

Use of crosslinking agents will provide a novel method that can modify the viscoelastic and elastic-plastic and durability properties of the tissue of the soft palate and other involved tissues and so ameliorate snoring and some cases of OSA. The method does not simply stiffen the tissue per se, but can also increase the damping coefficient and/or the damping ratio of the tissue in order to minimize oscillations. At the same time, the method can increase the strength, toughness, or fatigue resistance (resistance to degradation from repeated mechanical loading) of the tissue, or any combination thereof. Protein crosslinking can provide the added benefit of being less intrusive than the Pillar Procedure, and less harsh than the induction of scar tissue formation using both Snoreplasty and radiofrequency ablation. Protein crosslinking can also avoid damaging the molecular and/or micro-structural characteristics, and can prevent the detrimental long-term mechanical effects associated with these other procedures.

BRIEF DESCRIPTION OF THE DRAWINGS

For a more complete understanding of the present invention, reference is now made to the following descriptions taken in conjunction with the accompanying drawings, in which.

DETAILED DESCRIPTION

Figure 1:
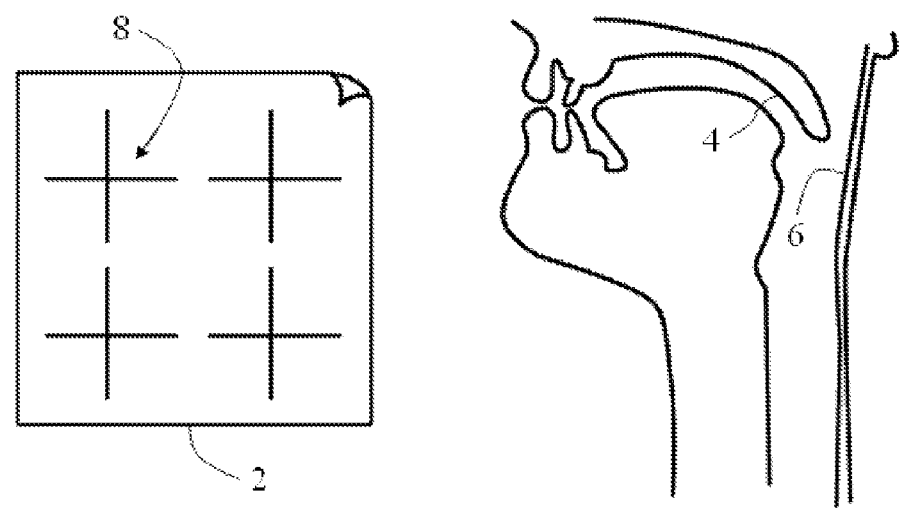
FIG. 1 is a schematic drawing showing use of a crosslinker-containing patch.

Protein crosslinking has been used to modulate both the mechanical properties and chemical stability of collagenous tissues (Charulatha and Rajaram, 2003; Chuang et al., 2007; Han et al., 2003; Slusarewicz et al., 2010b; Sung et al., 2001; Tang et al., 2008; Vasudev and Chandy, 1997; Zhai et al., 2006). Historically, crosslinking has been conducted ex vivo to modulate the strength and resistance to enzymatic degradation of tissue implants, and has been considered with respect to producing allografts for meniscal implant (Hunter et al., 2005), although approaches aimed at injection of crosslinkers in vivo are also being developed (Slusarewicz et al., 2010c).

An ideal crosslinker would be non-toxic and rapidly reactive, although more toxic and slower reacting crosslinkers could be considered provided that they were sufficiently safe and effective. Possible crosslinking reagents that could be used for the purposes of this invention include, but are not limited to: D- or L-Threose (Verzijl et al., 2002), genipin (Sung et al., 1999a; Sung et al., 1999b; Hedman et al., 2006; Sung et al., 1999b; Yerramalli et al., 2007), Methylglyoxal (Wagner et al., 2006), 1-ethyl-3-(3-dimethylaminopropyl)carbodiimide hydrochloride (EDC) (Gratzer and Lee, 2001), proanthocyanidin (Han et al., 2003) and glutaraldehyde (Wu et al., 2007; Yang et al., 2005; Hoffmann et al., 2009). In addition, different crosslinkers can exert different mechanical effects (Slusarewicz et al., 2010c). Thus, combinations of crosslinkers may also be incorporated into embodiments in order to modulate the final mechanical properties of the soft palate and/or pharynx tissue. Thus the solutions, sprays, patches and strips described herein may contain a mixture of two or more crosslinking agents.

In the various aspects of this invention, crosslinker treatment can be used either alone or as an adjunct to surgery. Crosslinker can be applied in the various forms described either before or during the surgical procedure or afterwards.

In one aspect, a solution of the crosslinking reagent, in a suitable carrier solution, is injected into the soft palate in a manner analogous to Snoreplasty, with no associated heating or fibrosis induction, or denaturation of the tissue in some embodiments. As the protein crosslinking reagent reacts with the tissue, it can induce the formation of crosslinks that modify the elastic-plastic and viscoelastic mechanical properties of the tissue including increasing the damping ratio and decreasing the oscillation magnitudes and vibration and undesired deformation of the palate. The crosslink augmentation can also increase the tissue's resistance to mechanical degradation. The reagent may be injected in one location in the palate or in a number of locations in order to facilitate its diffusion to the final desired distribution. The carrier solution may be aqueous or non-aqueous and may contain other non-crosslinking components that may help to facilitate crosslinking Such components include, but are not limited to, buffers (in order to provide and maintain a pH that is most optimal for the particular crosslinker being used), surfactants (in order to enhance the diffusion of the crosslinker within the tissue, and co-factors (that enhance the reactivity of the crosslinking reagent). The crosslinker may be administered to the patient only once or over a series of treatments. In the latter case, sequential administrations may be desirable in order to provide the individual patient only with the minimal amount of palate elastic-plastic and viscoelastic property modification (including increase in damping ratio) required to relieve their symptoms. The crosslinker can be selected from several known minimally toxic crosslinking agents such as genipin at a level of up to about 1200 micromoles and concentration of at least 5 mM (preferably about 20-100 mM) and the buffer can be about 25-250 mM EPPS 4-(2-Hydroxyethyl)-1-piperazinepropanesulfonic acid (EPPS) (preferably approximately 50 mM) at a pH of about 7-10 (preferably about 8) and optionally contain about 25-250 mM of a phosphate salt (preferably about 50 mM) to facilitate the crosslinking reaction and also optionally contain a co-solvent such as dimethyl sulfoxide (at about 1-50%, preferably about 10-20%) to increase the solubility of the crosslinker.

In some embodiments, the crosslinker can be genipin or methylglyoxal at a concentration of about 10 to 60 mM in about 50 mM 4-(2-Hydroxyethyl)-1-piperazinepropanesulfonic acid (EPPS) buffer, at about pH 9, with about 50 mM phosphate ions.

In another aspect, the crosslinking solution described above is administered to the patient in the form of an aerosol spray at crosslinker concentrations and in a buffered carrier similar to that described above. The crosslinker can then diffuse into the tissue of the palate in order to increase the damping coefficient and damping ratio and mechanically stabilize the tissue. The crosslinker can be delivered from a pump that is pressurized with a suitable gaseous or liquid propellant or one that is actuated using a hand pump. An advantage of this delivery system is that the crosslinker can be delivered without the need to create an incision in the tissue. In addition, the formulation may contain both thickening agents and bio-compatible adhesives that coat the surface of the palate to maintain contact of the crosslinker with the tissue over a prolonged period of time in order to facilitate its diffusion into the tissue. Suitable thickening agents might include, but are not limited to, natural polysaccharides such as gellan gum, alginates, agar, carrageenan and pectin, proteins such as gelatin and artificial molecules such as Carbomer (polyacrylic acid), polyethylene glycol. Non-limiting examples of suitable adhesives would be poly (glycerol-co-sebacate acrylate) (Mandavi et al., 2008), oleic methyl esters (Klapperich et al., 2009) or alkyl ester cyanoacrylates (Jonn et al., 2000).

In a further aspect, the crosslinking reagent is delivered via a patch that is placed on the surface of the soft palate. The crosslinker can be impregnated into the patch or incorporated into a delivery vehicle that coats the surface of the patch that is in contact with the tissue. The patch may also be coated with a bio-compatible adhesive such as those described above in order to maintain its attachment to the tissue. The patch may also be attached to the select tissue by biodegradable or semi-permanent sutures or by a tack or staple like device. The delivery vehicle could be either a suitable solvent, or solution containing appropriate excipients described with or without suitable thickening agents. The formulation may also optionally contain penetration enhancing reagents such as dimethyl sulfoxide in order to facilitate the entry of the crosslinker into the tissue. Alternatively the solution could be impregnated into the patch. The impregnated crosslinker could also be in a solid form which would dissolve slowly over time once in contact with bodily fluids, thereby providing a sustained release of crosslinker over time. In the case of non-degradable polymers the material of the patch would be porous and the patch would be removed by a clinician once its function has been completed. In some embodiments, the crosslinker is adhered to one side of the patch as part of a semi-solid formulation. The patch could be constructed of a bio-degradable material such as polylactic or polyglycolic acid which would then slowly dissolve with time and not have to be removed by a clinician. The crosslinker would then be slowly released from the patch as it dissolved. In the case of non-degradable polymer patches the patch could also be coated with a layer or multiple layers of bio-degradable polymer containing crosslinking reagent in order to provide a pool of slowly releasing crosslinker. Different concentrations of crosslinker can be used in these different layers of degradable polymer in order to control the release rates of the crosslinker over time. In all cases the patch could also be designed to allow airflow if the patch were inadvertently dislodged. To accommodate this function the patch could include a pattern of perforations and/or intersecting cut-lines that would enable portions (flaps) of the patch to deform if not in direct contact with tissue, facilitating airflow through the flap region. Alternately the patch could contain holes to facilitate airflow, or a combination of flaps and holes.

Solid or liquid crosslinker could be incorporated into the patch by addition to the molten polymer prior to casting, molding or spinning. Alternatively the crosslinker could be co-solubilized with the polymer in a suitable solvent (for example, acetone) and then incorporated into the device by removal of the solvent by evaporation or by precipitation (for example, by the addition of ethanol) of the polymer as described previously (Athanasiou et al., 1995; Singhal et al., 1996). The crosslinker and polymer could also be solubilized separately and mixed prior to precipitation in either the same solvent or different (miscible) solvents. Also, the solid crosslinker could also be mixed into the polymer gum formed by precipitation of solubilised polymer and prior to molding. The rate of crosslinker release can be controlled by varying the amount or concentration of the crosslinker incorporated into the device as well as by selecting polymers or other materials with differing in vivo degradation rates.

Degradation of bio-degradable polymers is also associated with a decrease of pH due to the production of acidic monomers. It has been shown that many protein crosslinkers act less efficiently at acidic pH (Slusarewicz et al., 2010a), and that this acidification process can be ameliorated by the incorporation of basic salts into the polymer matrix (Agrawal and Athanasiou, 1997). The biodegradable patches described above (and the strips described below) can also incorporate such basic salts in order to maximise the reactivity of the crosslinkers. Such salts could be inorganic (for example, but not limited to, calcium carbonate, calcium hydroxyapatite or sodium bicarbonate) or organic (for example, but not limited to, 2-Amino-2-hydroxymethyl-propane-1,3-diol (Tris) or 4-(2-hydroxyethyl)-1-piperazineethanesulfonic acid (HEPES). These basic salts can be incorporated at a level of about 5-50% by weight of the polymer (preferably about 15-30%).

The crosslinker can be selected from any of several known minimally toxic crosslinking agents such as genipin at a level of about 1-250 mg per patch (preferably about 5-50 mg). Additionally the patch can also optionally contain an alkaline salt such as calcium carbonate to maintain an elevated pH as the device degrades at a level of about 5-50% by weight of the polymer (preferably about 5-30%).

The crosslinker embedded into the patch may also be incorporated into a formulation that is designed to optimize its activity by the suitable adjustment or addition of, but not exclusively, pH, ionic strength, cations, anions, phosphate ions, and/or surfactants.

In addition to being applied to the soft palate, the patches described above could also be applied to the surfaces of the pharynx in order to crosslink, strengthen, increase resilience and toughness (energy required to create a non-recoverable deformation and to fail the tissue respectively), increase the mechanical fatigue resistance or resistance to repetitive mechanical loading, and otherwise mechanically modify the outer fibrous layer and thus help prevent the pharangeal collapse that occurs in many sufferers of OSA.

In another aspect, the crosslinker is incorporated into a non-degradable strip-type delivery device such as those used in a Pillar procedure of the soft palate. The crosslinker may be incorporated in any of the ways described above. Following implantation the crosslinker can diffuse into and can crosslink the tissue of the palate, and thus can serve to further assist in modifying the mechanical properties of the tissue including increasing the damping ratio, strength, toughness and/or fatigue resistance. The crosslinker can counteract the mechanical degradation of the tissue caused by the implant itself and the scarring that it induces. In this case the crosslinker provides a third mode of action for the device in order to improve its efficacy.

In addition the polymer of the strip could be constructed using a bio-degradable polymer, which can allow for the sustained release of crosslinker over time as well as the induction of biological scar tissue before complete dissolution of the strips themselves. The crosslinker can be any of several known minimally toxic crosslinking agents such as genipin or methylglyoxal at a level of about 1-20 mg per strip, though more can also be incorporated. Additionally the fixation device can also optionally contain an alkaline salt such as calcium hydroxyapatite to maintain an elevated pH as the device degrades at a level of about 5-50% by weight of the polymer (preferably about 15-30%).

The crosslinker embedded into the strips may also be incorporated into a formulation that is designed to optimize its activity by the suitable adjustment or addition of, but not exclusively, pH, ionic strength, cations, anions, phosphate ions, and/or surfactants.

In other aspects of this invention, crosslinker treatment in the form of injections, sprays or patches is combined with either the Pillar procedure or Snoreplasty in order to further enhance their effects. Crosslinker may be administered before, during or after the Pillar or Snoreplasty procedure.

The crosslinker delivery vehicles described herein are single-phase systems consisting of a solution of crosslinking reagent in either a solvent or a solvent containing various excipients and/or thickening agents. In another aspect, the carrier vehicle is comprised of a two-phase system such as an oil-in-water or a water-in-oil emulsion or micro-emulsion. Depending on the emulsion and the polarity of the crosslinker, the crosslinker may be incorporated into either the continuous or dispersed phases. The components of the emulsion may also be designed to enhance the penetration of the crosslinking into the tissue. The emulsion may also contain three or more phases, such as a water-in-oil-in-water (WOW) emulsion with the crosslinker incorporated into one or more than one of the phases as required. The formulations described here are not limited to simple emulsion systems and can also include more complex systems such as liposomal formulations and multi-vesicular emulsions.

In another aspect of the invention, the crosslinker is encapsulated into micro- or nano-spheres made from a polymeric material and which are suspended in either a single or multi-phase carrier vehicle. The beads serve as a reservoir for the sustained and controlled release of the crosslinking material into the tissue. The polymeric material is ideally bio-degradable but could alternatively be non-degradable.

FIG. 1 shows an embodiment in which a patch 2 of crosslinker embedded biodegradable material can be placed onto the surface of the soft palate 4 or pharynx 6 of a subject or patient with the aid of a suitable bio-compatible adhesive or a suture or a tack type device. Crosslinker is eluted from the patch over time to facilitate tissue stiffening and reduction in vibration or airway obstruction. Cross-shaped slits 8 are cut into the patch, which can then form flaps and openings to facilitate breathing should the patch become dislodged and enter the trachea. Alternatively the patch may be fabricated with holes to perform the same function, or a combination of holes and slits.

Figure 2:
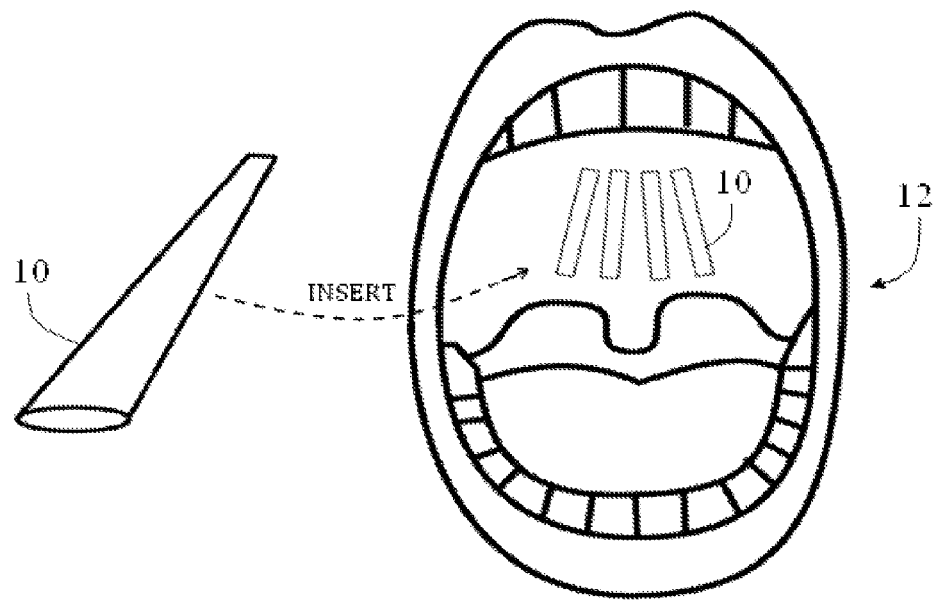
FIG. 2 is a schematic drawing showing use of a crosslinker-containing strip.

In another embodiment shown in FIG. 2, crosslinker-impregnated strips 10 of biodegradable polymer are inserted into the soft palate as viewed through the open mouth 12 of a subject or patient. Crosslinker is eluted from the strips over time to facilitate tissue stiffening, strengthening and reduction in palate vibration or airway obstruction The present invention may be better understood by referring to the accompanying examples, which are intended for illustration purposes only and should not in any sense be construed as limiting the scope of the invention.

EXAMPLE 1

One can treat a patient who suffers from excessive snoring or from OSA where airway blockage caused by the soft palate is a contributing factor by injecting a solution of 40 mM genipin in an alkaline solution such as 100 mM EPPS/ 100 mM sodium phosphate buffer at pH 9, or a higher concentration of genipin in a similar buffer further supplemented with dimethyl sulfoxide or a solution of 100 mM methylglyoxal in a similar buffer. This injection can be performed with a large volume at a single location in the palate or in multiple locations using smaller volumes to obtain sufficient coverage of the tissue.

EXAMPLE 2

One can treat patients suffering from snoring or from OSA where airway constriction is a contributing factor, by applying a solution of crosslinker as described in Example 1 to either the soft palate or the surface of the pharynx in the form of an aerosolized spray. The spray could be delivered from either a self-contained pressurized container, an actuated pump or from a device where the pressurized propellant is supplied from a separate vessel to that in which the crosslinker is contained.

EXAMPLE 3

One can treat patients suffering from snoring or from OSA where airway constriction is a contributing factor, by applying a patch composed of the biodegradable polymer, polylactic acid to either the soft palate of the surface of the pharynx respectfully. The patch is constructed by dispersing solid genipin crosslinker to the liquid polymer during manufacture at a ratio of 10 mg of genipin to 1 g of poly lactic acid. Following application, crosslinker is released as the patch is dissolved and can then penetrate into the tissue to which the patch has been applied.

EXAMPLE 4

One can treat a patient who suffers from excessive snoring or from OSA where airway blockage caused by the soft palate is a contributing factor by implanting non-degradable fibrous strips, for example such as the polystyrene strips used in the Pillar Procedure into the soft palate, coated with a layer of degradable polymer impregnated with crosslinking agent. These strips are coated by either immersing them in a molten polymer containing a dispersed crosslinking agent such as genipin at a concentration of 10 mg per gram of polymer, or by sequential immersions in a solution of containing 50 mM genipin and a saturating concentration of the biodegradable polymer solubilized in a suitable solvent such as ethyl acetate and subsequent evaporation of the solvent.

EXAMPLE 5

One can treat a patient who suffers from excessive snoring or from OSA where airway blockage caused by the soft palate is a contributing factor by conducting the Pillar Procedure immediately followed by injecting a solution of 40 mM genipin in an alkaline solution such as 100 mM EPPS/100 mM sodium phosphate buffer at pH 9 into the soft palate.

EXAMPLE 6

A patient suffering from OSA can be surgically treated by uvulopalatopharyngoplasty and then further treated by; (a) affixing a patch as described in Example 3 to the surface of the pharynx or soft palate, (b) injecting a solution as described in Example 1 into the soft palate, (c) applying a spray as described in Example 2 to the soft palate or pharynx or (d) by implanting crosslinker impregnated strips such as those described in Example 4 into the soft palate.

EXAMPLE 7

One can treat a patient who suffers from excessive snoring or from OSA where airway blockage caused by the soft palate is a contributing factor by co-injecting into the soft palate a solution of 40 mM genipin in an alkaline solution such as 100 mM EPPS/100 mM sodium phosphate buffer at pH 9 with a sclerosant such as sodium tetradecyl sulfate.

EXAMPLE 8

The improvement in soft palate mechanical properties including increase in the damping ratio due to the present methods and devices can be measured using human or bovine cadaveric soft palate explants and in vitro experimental methods briefly summarized here. An appropriate number of tissue specimens are included in the study according to previously documented variances in mechanical properties of the selected tissue type. The specimens are randomly divided into a crosslinking treatment group and a buffer only sham treatment group. The crosslinked specimens each receive a 0.5 ml injection of 40 mM genipin in 100 mM EPPS/100 mM sodium phosphate buffer at pH 9 using a small, greater than 20 gauge, or insulin-sized needle. The sham group receives 0.5 ml injections of buffer only. The anterior bony portion of the palate is potted or clamped and mounted in a simple variable flow wind tunnel to simulate physiologic airflow at various velocities across the soft palate. Specimen displacements can be measured in a variety of ways. Preferably the measurements are made with a non-contact laser caliper with data collection rate of at least 10 Hz. Oscillation magnitudes and frequencies of the tip of the soft palate are calculated. The data is normalized using the specimen's cross-sectional area measured with a rotating laser micrometer. Comparisons between treatment groups can be made using a Mann-Whitney non-parametric comparison of means. Additionally, before and after crosslinking treatment measurements can also be made using the sham treatment group by subjecting it to buffered genipin injection subsequent to initial testing (post-sham injection). Post-crosslinking-treatment test data can then be compared to pre-treatment data using a paired statistical analysis such as the Wilcoxon non-parametric paired analysis. The effect of the crosslinking treatment is evidenced by a statistically significant and greater than 20%:a) increase in damping coefficient or damping ratio, or b) decrease in peak displacement.

The following publications are incorporated by reference herein in their entirety.
1. Agrawal, C. M. and K. A. Athanasiou. 1997. Technique to control pH in vicinity of biodegrading PLA-PGA implants. *J. Biomed. Mater. Res.* 38:105-114.
2. Athanasiou, K. A., A. R. Singhal, C. M. Agrawal, and B. D. Boyan. 1995. In vitro degradation and release characteristics of biodegradable implants containing trypsin inhibitor. *Clin. Orthop. Relat Res.* 272-281.
3. Blumen, M. B., S. Dahan, B. Fleury, C. Hausser-Hauw, and F. Chabolle. 2002. Radiofrequency ablation for the treatment of mild to moderate obstructive sleep apnea. *Laryngoscope* 112:2086-2092.
4. Brietzke, S. E. and E. A. Mair. 2001. Injection snoreplasty: how to treat snoring without all the pain and expense. *Otolaryngol. Head Neck Surg.* 124:503-510.
5. Brietzke, S. E. and E. A. Mair. 2003. Injection snoreplasty: extended follow-up and new objective data. *Otolaryngol. Head Neck Surg.* 128:605-615.
6. Brietzke, S. E. and E. A. Mair. 2004. Injection snoreplasty: investigation of alternative sclerotherapy agents. *Otolaryngol. Head Neck Surg.* 130:47-57.
7. Catalano, P., Y. H. Goh, and J. Romanow. 2007. Additional palatal implants for refractory snoring. *Otolaryngol. Head Neck Surg.* 137:105-109.
8. Charulatha, V. and A. Rajaram. 2003. Influence of different crosslinking treatments on the physical properties of collagen membranes. *Biomaterials* 24:759-767.
9. Chuang, S. Y., R. M. Odono, and T. P. Hedman. 2007. Effects of exogenous crosslinking on in vitro tensile and compressive moduli of lumbar intervertebral discs. *Clin. Biomech.* 22:14-20.
10. Fischer, Y., B. Hafner, and W. J. Mann. 2000. [Radiofrequency ablation of the soft palate (somnoplasty). A new method in the treatment of habitual and obstructive snoring]. *HNO* 48:33-40.
11. Friedman, M., R. Vidyasagar, D. Bliznikas, and N. J. Joseph. 2006. Patient selection and efficacy of pillar 11. implant technique for treatment of snoring and obstructive sleep apnea/hypopnea syndrome. *Otolaryngol. Head Neck Surg.* 134:187-196.
12. Gratzer, P. F. and J. M. Lee. 2001. Control of pH alters the type of cross-linking produced by 1-ethyl-3-(3-dimethylaminopropyl)-carbodiimide (EDC) treatment of acellular matrix vascular grafts. *J. Biomed. Mater. Res.* 58:172-179.
13. Guilleminault, C., R. Stoohs, and S. Duncan. 1991. Daytime sleepiness in regular snorers. *Chest* 99:40-49.
14. Guilleminault, C., A. Tilkian, and W. C. Dement. 1976. The sleep apnea syndromes. *Annu. Rev. Med.* 27:465-484.
15. Han, B., J. Jaurequi, B. W. Tang, and M. E. Nimni. 2003. Proanthocyanidin: a natural crosslinking reagent for stabilizing collagen matrices. *J. Biomed. Mater. Res. A* 65:118-124.
16. Hedman, T. P., H. Saito, C. Vo, and S. Y. Chuang. 2006. Exogenous cross-linking increases the stability of spinal motion segments. *Spine* 31:480-485.
17. Hoffmann, B., D. Seitz, A. Mencke, A. Kokott, and G. Ziegler. 2009. Glutaraldehyde and oxidised dextran as crosslinker reagents for chitosan-based scaffolds for cartilage tissue engineering. *J. Mater. Sci. Mater. Med.* 20:1495-1503.
18. Hunter, S. A., F. R. Noyes, B. Haridas, M. S. Levy, and D. L. Butler. 2005. Meniscal material properties are minimally affected by matrix stabilization using glutaraldehyde and glycation with ribose. *J. Orthop. Res.* 23:555-561.
19. Jonn, J. Y., J. Bobo, J. Quintero, and J. P. Moseley. Absorbable adhesive compositions. [6620846]. 2000. US. Ref Type: Patent
20. Klapperich, C. M., C. L. Noack, J. D. Kaufman, L. Zhu, L. Bonnaillie, and R. P. Wool. 2009. A novel biocompatible adhesive incorporating plant-derived monomers. *J. Biomed. Mater. Res. A* 91:378-384.
21. Lowe, A. A. 1994. Dental appliances for the treatment of snoring and/or obstructive sleep apnea. In Principles and practice of sleep medicine. M. Kryger, T. Roth, and W. Dement, editors. WB Saunders Co., 722-735.
22. Mandavi, A., L. Ferreira, C. Sundback, J. W. Nichol, E. P. Chan, D. J. Carter, C. J. Bettinger, S. Patanavanich, L. Chignozha, E. Ben-Joseph, A. Galakatos, H. Pryor, I. Pomerantseva, P. T. Masiakos, W. Faquin, A. Zumbuehl, S. Hong, J. Borenstein, J. Vacanti, R. Langer, and J. M. Karp. 2008. A biodegradable and biocompatible gecko-inspired tissue adhesive. *Proc. Natl. Acad. Sci. U.S.A* 105:2307-2312.
23. Romanow, J. H. and P. J. Catalano. 2006. Initial U.S. pilot study: palatal implants for the treatment of snoring. *Otolaryngol. Head Neck Surg.* 134:551-557.
24. Sanders, M. H. 1990. The management of sleep-disordered breathing. In Cardiorespiratory disorders during sleep. R. J. Martin, editor. Futura, Mount Kisco, N.Y. 141-187.
25. Schmidt-Nowara, W., A. Lowe, L. Wiegand, R. Cartwright, F. Perez-Guerra, and S. Menn. 1995. Oral appliances for the treatment of snoring and obstructive sleep apnea: a review. *Sleep* 18:501-510.
26. Singhal, A. R., C. M. Agrawal, and K. A. Athanasiou. 1996. Salient Degradation Features of a 50:50 PLA/PGA Scaffold for Tissue Engineering. *Tissue Eng* 2:197-207.
27. Slusarewicz, P., K. Zhu, and T. Hedman. 2010a. Kinetic characterization and comparison of various protein cross-linking reagents for matrix modification. *J. Mater. Sci. Mater. Med.* 21:1175-1181.
28. Slusarewicz, P., K. Zhu, and T. P. Hedman. 2010b. Kinetic Characterization and Comparison of Various Protein Crosslinking Reagents for Matrix Modification. *J. Mater. Sci. Mater. Med.* DOI: 10.1007/s10856-010-3986-8.
29. Slusarewicz, P., K. Zhu, B. Kirking, J. Toungate, and T. Hedman. 2010c. Optimization of Protein Crosslinking Formulations for the Treatment of Degenerative Disc Disease. *Spine* In Press.
30. Sung, H. W., Y. Chang, C. T. Chiu, C. N. Chen, and H. C. Liang. 1999a. Crosslinking characteristics and mechanical properties of a bovine pericardium fixed with a naturally occurring crosslinking agent. *J. Biomed. Mater. Res.* 47:116-126.
31. Sung, H. W., Y. Chang, C. T. Chiu, C. N. Chen, and H. C. Liang. 1999b. Mechanical properties of a porcine aortic valve fixed with a naturally occurring crosslinking agent. *Biomaterials* 20:1759-1772.
32. Sung, H. W., I. L. Liang, C. N. Chen, R. N. Huang, and H. F. Liang. 2001. Stability of a biological tissue fixed with a naturally occurring crosslinking agent (genipin). *J. Biomed. Mater. Res.* 55:538-546.
33. Tang, S. Y., A. D. Sharan, and D. Vashishth. 2008. Effects of collagen crosslinking on tissue fragility. *Clin. Biomech.* (*Bristol., Avon.*) 23:122-123.
34. Vasudev, S. C. and T. Chandy. 1997. Effect of alternative crosslinking techniques on the enzymatic degradation of bovine pericardia and their calcification. *J. Biomed. Mater. Res.* 35:357-369.
35. Verzijl, N., J. De Groot, Z. C. Ben, O. Brau-Benjamin, A. Maroudas, R. A. Bank, J. Mizrahi, C. G. Schalkwijk, S. R. Thorpe, J. W. Baynes, J. W. Bijlsma, F. P. Lafeber, and J. M. te Koppele. 2002. Crosslinking by advanced glycation end products increases the stiffness of the collagen network in human articular cartilage: a possible mechanism through which age is a risk factor for osteoarthritis. *Arthritis Rheum.* 46:114-123.
36. Wagner, D. R., K. M. Reiser, and J. C. Lotz. 2006. Glycation increases human annulus fibrosus stiffness in both experimental measurements and theoretical predictions. *J. Biomech.* 39:1021-1029.
37. Wu, X., L. Black, G. Santacana-Laffitte, and C. W. Patrick, Jr. 2007. Preparation and assessment of glutaraldehyde-crosslinked collagen-chitosan hydrogels for adipose tissue engineering. *J. Biomed. Mater. Res. A* 81:59-65.
38. Yang, S. H., C. K. Hsu, K. C. Wang, S. M. Hou, and F. H. Lin. 2005. Tricalcium phosphate and glutaraldehyde crosslinked gelatin incorporating bone morphogenetic protein—a viable scaffold for bone tissue engineering. *J. Biomed. Mater. Res. B Appl. Biomater.* 74:468-475.
39. Yerramalli, C. S., A. I. Chou, G. J. Miller, S. B. Nicoll, K. R. Chin, and D. M. Elliott. 2007. The effect of nucleus pulposus crosslinking and glycosaminoglycan degradation on disc mechanical function. *Biomech. Model. Mechanobiol.* 6:13-20.
40. Zhai, W., J. Chang, K. Lin, J. Wang, Q. Zhao, and X. Sun. 2006. Crosslinking of decellularized porcine heart valve matrix by procyanidins. *Biomaterials* 27:3684-3690.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the invention and the following claims.

What is claimed is:

1. A method of treating snoring and/or obstructive sleep apnea in a subject in need of such treatment, comprising decreasing oscillation magnitude and flaccidity of the subject's soft palate or pharynx tissue, when the tissue is subjected to physiologic airflow, by crosslinking tissue proteins within the tissue,
wherein the crosslinking comprises contacting the soft palate or pharynx tissue with a crosslinking reagent.

2. The method of claim 1, wherein crosslinking occurs without heating, contracting, inducing fibrosis, or denaturing of the tissue, or any combination thereof.

3. The method of claim 1, wherein the crosslinking reagent is delivered to the tissue via injection, spraying, a patch, a strip-type delivery device, or any combination thereof.

4. The method of claim 3, wherein the injecting or spraying is of a liquid, emulsion or micro-emulsion.

5. The method of claim 3, wherein the patch or delivery device is biodegradable or non-biodegradable.

6. The method of claim 5, wherein the patch or delivery device is non-biodegradable and porous, and the crosslinker is embedded within the pores.

7. The method of claim 5, wherein the patch is non-biodegradable and the crosslinker is adhered to one side of the patch as part of a semi-solid formulation.

8. The method of claim 5, wherein the patch or delivery device is biodegradable and comprises a basic salt.

9. The method of claim 8, wherein the salt is calcium carbonate, calcium hydroxyapatite, sodium bicarbonate, 2-Amino-2-hydroxymethyl-propane-1,3-diol (Tris) or 4-(2-hydroxyethyl)-1-piperazineethanesulfonic acid (HEPES).

10. The method of claim 5, wherein the patch or delivery device is coated with one or more layers of crosslinker-containing biodegradable polymer.

11. The method of claim 10, wherein each layer comprises a basic salt.

12. The method of claim 11, wherein the salt is calcium carbonate, calcium hydroxyapatite, sodium bicarbonate, 2-Amino-2-hydroxymethyl-propane-1,3-diol (Tris) or 4-(2-hydroxyethyl)-1-piperazineethanesulfonic acid (HEPES).

13. The method of claim 10, wherein the patch or delivery device is coated with multiple layers of crosslinker-containing biodegradable polymer, and the crosslinker varies from layer to layer.

14. The method of claim 5, wherein the patch is affixed to the tissue with a bio-compatible adhesive.

15. The method of claim 14, wherein the adhesive is poly(glycerol-co-sebacate acrylate), an oleic methyl ester or an alkyl ester cyanoacrylate.

16. The method of claim 1, wherein the crosslinking reagent comprises one or more of the following crosslinkers: genipin, methylglyoxal, L-threose, D-threose, proanthocyanidin, EDC, or glutaraldehyde.

17. The method of claim 16, wherein the crosslinker is genipin and wherein said genipin is at a concentration of about 10 to 60 mM in about 50 mM 4-(2-Hydroxyethyl)-1-piperazinepropanesulfonic acid (EPPS) buffer at about pH 9 with about 50 mM phosphate ions.

18. The method of claim 16, wherein the crosslinker is methylglyoxal and wherein said methylglyoxal is at a concentration of about 10-60 mM in about 50 mM 4-(2-Hydroxyethyl)-1-piperazinepropanesulfonic acid (EPPS) buffer at about pH 9 with about 50 mM phosphate ions.

* * * * *